(12) United States Patent
Cho et al.

(10) Patent No.: US 9,357,795 B2
(45) Date of Patent: Jun. 7, 2016

(54) FLAVOR CONTAINING L-GLUTAMIC ACID AND METHOD THEREOF

(71) Applicant: CJ CHEILJEDANG CORPORATION, Seoul (KR)

(72) Inventors: Jin Man Cho, Seongnam-si (KR); Jeong Hwan Kim, Seoul (KR); Yong Bum Seo, Gimpo-si (KR); Jang Hee Park, Seoul (KP); In Seok Hwang, Seoul (KR); Hyun Suk Eom, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 13/673,850

(22) Filed: Nov. 9, 2012

(65) Prior Publication Data
US 2013/0122141 A1 May 16, 2013

(30) Foreign Application Priority Data
Nov. 10, 2011 (KR) .................. 10-2011-0116866

(51) Int. Cl.
| A23L 1/22 | (2006.01) |
| A23L 1/228 | (2006.01) |
| A23L 1/23 | (2006.01) |
| C12P 13/14 | (2006.01) |

(52) U.S. Cl.
CPC ............ *A23L 1/22091* (2013.01); *A23L 1/228* (2013.01); *A23L 1/23* (2013.01); *C12P 13/14* (2013.01)

(58) Field of Classification Search
USPC ................. 426/7, 650; 435/106, 107, 252.33; 562/573
See application file for complete search history.

(56) References Cited

U.S. PATENT DOCUMENTS

| 3,123,537 A | * | 3/1964 | Miescher et al. | ............. 435/110 |
| 3,220,929 A | | 11/1965 | Kinoshita et al. | |
| 3,281,247 A | * | 10/1966 | Miescher | ......................... 426/48 |
| 3,563,857 A | | 2/1971 | Oki et al. | |
| 3,616,224 A | * | 10/1971 | Shiio et al. | ..................... 435/106 |
| 3,713,848 A | * | 1/1973 | Katz et al. | ..................... 426/535 |
| 5,907,059 A | * | 5/1999 | Cami et al. | ..................... 562/573 |
| 2005/0214911 A1 | * | 9/2005 | Marchenko et al. | .......... 435/106 |

FOREIGN PATENT DOCUMENTS

| CN | 101801217 A | 8/2010 |
| JP | 32-9393 B1 | 11/1957 |
| JP | 54-086692 A | 10/1979 |
| JP | 5-244970 A | 9/1993 |
| KR | 10-0513996 B1 | 12/2005 |
| KR | 10-0824457 B1 | 4/2008 |
| KR | 10-2010-0017581 A | 2/2010 |
| WO | 2009-040150 A1 | 4/2009 |

OTHER PUBLICATIONS

NPL MSG: by Chiaki Sano entitled "History of Glutamate production" in Am. J. Clin. Nutr. 2009, 90(3): 728S-732S.*
Kikuchi,M., et al., Biotechnology of Amino Acid Production, progress in industrial microbiology, vol. 24, pp. 101-116, Kodansha Ltd. Tokyo, 1986.
Manual of Methods for General Bacteriology, Chapter II, Sections 6-11, pp. 65-207, American Society for Bacteriology, Washington D.C., USA, 1981.
Fermentative prodn. of L-glutamic acid—using glucose or sucrose-consuming bacteria in aerobic conditions, at a constant PH level and specified ammonium ion concn. JP 54086692A, n/a, DWPI, vol. DW197934, Abstract, Dec. 12, 1979.
Office Action dated Sep. 11, 2013 of corresponding Chinese Patent Application 201210449491.9—9 pages.

* cited by examiner

*Primary Examiner* — Michele L Jacobson
*Assistant Examiner* — Bhaskar Mukhopadhyay
(74) *Attorney, Agent, or Firm* — Knobbe Martens Olson & Bear LLP

(57) ABSTRACT

Disclosed herein is a method for producing a flavoring containing L-glutamic acid derived from natural foods by adjusting the content of ammonia remaining in a final fermentation broth after completion of culture to be in the range of 0 to 10 g/L in cultivation of L-glutamic acid producing microorganisms, thereby facilitating drying of the fermentation liquor containing L-glutamic acid. A flavoring produced by the method is also disclosed.

15 Claims, 1 Drawing Sheet

US 9,357,795 B2

FLAVOR CONTAINING L-GLUTAMIC ACID AND METHOD THEREOF

TECHNICAL FIELD

The present invention relates to a method for producing a flavoring containing L-glutamic acid and a flavoring produced by the method.

BACKGROUND ART

L-glutamic acid is a representative amino acid produced by fermentation. L-glutamic acid has a distinctive taste and is thus used broadly not only in the food industry, but also in the fields of medicine, animal feed, and the like.

L-glutamic acid can be produced using L-glutamic acid producing microorganisms. Examples of conventional methods for producing L-glutamic acid include a method of using glutamic acid producing bacteria of so-called coryneform belonging to the genera of *Brevibacterium, Corynebacterium, Microbacterium*, and variants thereof ("Amino Acid Fermentation", Gakkai Shuppan Center, pp. 195-215, 1986); a method of using microorganisms belonging to *Bacillus, Streptomyces, Penicillium* genera, and the like (U.S. Pat. No. 3,220,929); a method of using microorganisms belonging to *Pseudomonas, Arthrobacter, Serratia, Candida* genera, and the like (U.S. Pat. No. 3,563,857); a method of using *Aerobacter aerogenes* (now referred to as *Enterobacter aerogenes*) (Japanese Patent No. 32-9393 (1957)); and a method of using variant strains of *Echerichia coli* (Japanese Laid-Open Publication No. 5-244970 (1993)), and the like.

As known in the art, conventional methods for producing L-glutamic acid using microorganisms including the aforementioned methods generally include fermentation using microorganisms; accumulating L-glutamic acid in the fermentation liquor in a high concentration; purifying the fermentation liquor to provide L-glutamic acid with high purity; and crystallizing the obtained L-glutamic acid.

Such methods in the art require purification and crystallization of L-glutamic acid. This means that significantly many chemicals are used to carry out these processes, which is not compatible with recent consumer demand for health foods.

To resolve these problems, studies have focused on methods for producing L-glutamic acid without purifying or crystallizing fermentation liquors containing L-glutamic acid. For instance, there has been an attempt to obtain a flavoring using food grade chemicals to be utilized in fermentation of L-glutamic acid without conducting any purification and crystallization and drying the fermentation liquor, from which only microorganism sludge is removed (International Publication No. WO 2009/040150). Such an attempt is to provide a flavoring derived from natural foods having enhanced taste while reflecting the recent preferences by means of excluding the use of industrial chemicals and only using raw materials derived from natural foods.

However, the method disclosed in WO 2009/040150 uses pH modifiers and ammonia as a nitrogen source in the same manner as in conventional fermentation, and does not allow efficient drying of fermentation liquors, thereby making it difficult to adopt the method. Accordingly, there is a need for a process for easily drying fermentation liquors containing L-glutamic acid.

Examples of conventional methods for producing L-glutamic acid are disclosed in Korean Patent Nos. 10-0513996 and 10-0824457, Korean Patent Publication No. 10-2010-0017581A, and the like. All of these methods are aimed at mass production of L-glutamic acid, such as methods for producing L-glutamic acid using genetically engineered L-glutamic acid producing microorganisms, methods for producing L-glutamic acid through continuous fermentation processes, and the like. However, there has been no disclosure regarding a method for producing L-glutamic acid without conducting any purification and/or crystallization steps requiring enormous chemicals by facilitating drying of fermentation liquor containing L-glutamic acid.

DISCLOSURE

Technical Problem

In the fermentation process of microorganisms to produce L-glutamic acid, ammonia is generally used as a nitrogen source and/or a pH modifier. The present inventors recognized that the ammonia used in the microorganisms' fermentation process bound with glutamic acid in the course of concentration and drying of the fermentation liquor to form an ammonium salt, which inhibited drying of the fermentation liquor. In an effort to resolve this problem, the inventors have developed a method for producing a flavoring containing L-glutamic acid derived from natural food by excluding the use of ammonia or by using ammonia at an early stage of cultivation of microorganisms and, at a certain time period of cultivation of microorganisms, by using another pH modifier instead of ammonia (if necessary, supply separate nitrogen sources), such that the content of ammonia remaining in the final culture media after completion of culture is 0 to 10 g/L, which facilitated drying of the fermentation liquor containing L-glutamic acid.

The present invention is aimed at providing a method for producing a flavoring containing L-glutamic acid derived from natural foods, in which drying of a fermentation liquor containing L-glutamic acid is easily performed.

The present invention is also aimed at providing a flavoring containing L-glutamic acid derived from natural foods produced by the method of the present invention and having good dry properties.

Technical Solution

The present invention relates to a method for producing a flavoring containing L-glutamic acid derived from natural foods by adjusting the content of ammonia remaining in a final fermentation liquor after completion of culture to be in the range of 0 to 10 g/L in cultivation of L-glutamic acid producing microorganisms, thereby facilitating drying of the fermentation liquor containing L-glutamic acid, and a flavoring produced by the method.

One aspect of the present invention provides a method for producing a flavoring containing L-glutamic acid derived from natural foods, which includes: a) culturing an L-glutamic acid producing microorganism in a medium containing a carbon source, a nitrogen source and a pH modifier such that the content of ammonia remaining in a final fermentation broth after completion of culture is 0 to 10 g/L; b) after culturing, removing microorganism sludge from the final fermentation broth to yield a fermentation liquor; and c) drying the fermentation liquor from which the microorganism sludge has been removed.

Another aspect of the present invention provides a flavoring containing L-glutamic acid derived from natural foods produced by the method of the present invention.

Advantageous Effects

The present invention can facilitate drying of fermentation liquors containing L-glutamic acid in production of a flavoring containing L-glutamic acid derived from natural foods.

In addition, the present invention can facilitate drying of fermentation liquors containing L-glutamic acid, thereby providing a flavoring containing L-glutamic acid derived from natural foods having low moisture content, in more detail, having a moisture content of 0.5 wt % to 5 wt %.

MODE FOR INVENTION

Figure 1:
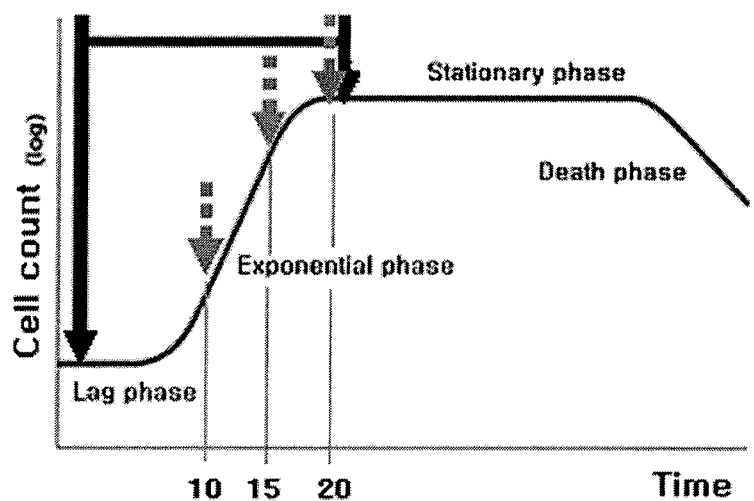
FIG. 1 is a graph depicting the growth curve of microorganisms on which the time to exchange sodium hydroxide in Example 1 (Table 1) is indicated (here, the arrow in solid line represents the range of time where the exchange of sodium hydroxide can be performed)

Hereinafter, embodiments of the present invention will be described in more detail with reference to the accompanying drawings. A description of details apparent to those skilled in the art will be omitted herein.

L-Glutamic Acid Producing Microorganisms

As microorganisms to be used in the present invention, mention can be made of any L-glutamic acid producing microorganisms without particular limitation and microorganisms known in the related art may also be used in the present invention. Examples of L-glutamic acid producing microorganisms include the genera of *Corynebacterium, Brevibacterium, Microbacterium, Bacillus, Streptomyces, Penicillium, Pseudomonas, Arthrobacter, Serratia, Candida* and *Echerichia* or their variants. For example, *Corynebacterium glutamicum* may be used in the present invention.

Media for Culturing Microorganisms (Media for Fermenting L-Glutamic Acid)

As culture media to be used in the present invention, mention can be made of any media capable of growing L-glutamic acid producing microorganisms without particular limitation and any media known in the related art or similar technical fields may also be used in the present invention.

The culture media may contain a sugar source, a nitrogen source, a phosphor source, a pH modifier, other mineral salts, and the like. These materials may be additionally added to the culture media in order to appropriately adjust culture conditions such as nutrients, pH and the like in the course of culturing microorganisms. The sugar source, nitrogen source, phosphor source, pH modifier, other mineral salts and the like may be food grade. The sorts of these materials are not particularly limited and any materials known in the related art or similar technical fields may be used. Examples thereof are as follows:

1) Sugar Source

Examples of sugar sources to be used in the present invention include, for example, sugars such as glucose, saccharose, lactose, fructose, maltose, starch, and cellulose; saccharized starch solution comprising the sugars as mentioned above; molasses such as sweet potato molasses, sugar beet molasses, and stem molasses; fats such as soy bean oil, sunflower oil, castor oil, coconut oil, and the like; fatty acids such as palmitic acid, stearic acid and linoleic acid; alcohols such as glycerol and ethanol; organic acids such as acetic acid. These materials may be used alone or in combination of two or more thereof.

2) Nitrogen Source

Examples of nitrogen sources to be used in the present invention include, for example, ammonium salts such as ammonium sulfate, ammonium chloride, ammonium phosphate, ammonium carbonate, ammonium nitrate; ammonia; urea; nitrates; amino acids; peptides; proteins; yeast extracts; corn saccharized solutions and the like. These materials may be used alone or in combination of two or more thereof.

3) Phosphor Source

Examples of phosphor sources to be used in the present invention include, for example, potassium dihydrogen phosphate, dipotassium hydrogen phosphate or corresponding sodium-containing salts. These materials may be used alone or in combination of two or more thereof.

4) pH Modifier

Examples of pH modifiers to be used in the present invention include, for example, ammonia, alkaline sodium salts or alkaline potassium salts, and the like. Examples of the alkaline sodium salts include sodium hydroxide, sodium hydrogen carbonate ($NaHCO_3$), sodium acetate, sodium metasilicate ($Na_2SiO_3$), and the like. Examples of the alkaline potassium salts include potassium hydroxide, potassium carbonate, and the like. These materials may be used alone or in combination of two or more thereof.

The culture media to be used in the present invention may contain materials required for growth of microorganisms. Examples of such materials include magnesium slats such as magnesium sulfate; ferric salts such as iron sulfate; and metal salts such as manganese salts. Further, the culture media may comprise essential growth substances such as amino acids and/or vitamins.

The conditions for culturing microorganisms of the present invention are not particularly limited and general conditions for culturing L-glutamic acid producing microorganisms may be utilized. For example, when using a strain belonging to genus *Corynebacterium*, suitable media for culturing the strain are known in Manual of Methods for General Bacteriology, Amerimay Society for Bacteriology (Washington D.C., USA, 1981).

The temperature of culturing solution preferably ranges from 20° C. to 45° C., more preferably from 25° C. to 45° C.

The term "fermentation broth" as used herein has the same meaning as a culture solution of L-glutamic acid producing microorganisms.

Methods for obtaining L-glutamic acid from L-glutamic acid producing microorganisms are not particularly limited, but any method known in the related art may be used. One example of such methods, but not limited thereto, is carried out by inoculating an L-glutamic acid producing microorganism in a suitably prepared culture medium, culturing the strain for a certain period of time, and treating the culture medium with a surfactant when the microorganism arrives at a certain degree of growth, thereby inhibiting the growth of L-glutamic acid producing strains while inducing extracellular discharge of L-glutamic acid at the same time.

The growth phases of microorganisms consist of Lag phase, Exponential phase, Stationary phase and Death phase (See FIG. 1).

In one aspect, the present invention provides a method for producing a flavoring containing L-glutamic acid derived from natural foods comprising: a) culturing an L-glutamic acid producing microorganism in a medium containing a carbon source, a nitrogen source and a pH modifier such that the content of ammonia remaining in a final fermentation broth after completion of culture is 0 to 10 g/L; b) after culturing, removing microorganism sludge from the final fermentation broth to yield a fermentation liquor; and c) drying the fermentation liquor from which the microorganism sludge is removed.

When the content of ammonia remaining in the final fermentation broth after completion of culture of the L-glutamic acid producing microorganism is greater than 10 g/L, L-glutamic acid and ammonia bind to form ammonium salts in a fermentation liquor, thereby inhibiting drying of the fermentation liquor, which makes the production of dried L-glutamic acid difficult.

In step a), in order to adjust the content of ammonia remaining in the final fermentation broth after completion of culture to be 0 to 10 g/L, cultivation of the microorganisms may be performed using other nitrogen sources and/or pH modifiers except for ammonia as a nitrogen source and/or a pH modifier.

Examples of other nitrogen sources except for ammonia include ammonium salts such as ammonium sulfate, ammonium chloride, ammonium phosphate, ammonium carbonate, ammonium nitrate; urea; nitrates; amino acids; peptides; proteins; yeast extracts; corn saccharized solutions, and the like. These materials may be used alone or in combination of two or more thereof.

Examples of other pH modifiers except for ammonia include alkaline sodium salts such as sodium hydroxide, sodium hydrogen carbonate ($NaHCO_3$), sodium acetate, sodium metasilicate ($Na_2SiO_3$), and the like; and alkaline potassium salts such as potassium hydroxide, potassium carbonate, and the like. These materials may be used alone or in combination of two or more thereof. More preferably, sodium hydroxide is used.

When ammonia is used as a nitrogen source and/or a pH modifier in step a), cultivation may be performed by suitably adjusting ammonia amount used and/or a period of used time such that the content of ammonia remaining in the final fermentation broth after completion of culture is 0 to 10 g/L.

If ammonia is used as a nitrogen source and/or a pH modifier in step a), cultivation may be carried out using ammonia at an early stage of cultivation and then replacing the ammonia with other pH modifiers except for ammonia at the Lag phase to early Stationary phase of growth curve of L-glutamic acid producing strain to adjust the content of ammonia remaining in the final fermentation broth after completion of culturing to be in the range of 0 to 10 g/L.

Since ammonia used in the culture of microorganisms acts as a pH modifier as well as a nitrogen source, if ammonia is replaced with other pH modifiers at the early stage of cultivation, it can cause insufficient nitrogen sources required in growth and basal metabolism, thereby adversely affecting fermentation of L-glutamic acid. Accordingly, it is preferred to replace ammonia at Lag phase to early Stationary phase of growth curve of L-glutamic acid producing strain.

In the case where other pH modifiers than ammonia are used at a certain degree of growth of L-glutamic acid producing strain in step a), if necessary, separate nitrogen sources except for ammonia may be additionally added.

In step b), the removal of microorganism sludge from the final fermentation broth is not particularly limited and any method known in the related art may be used. Preferably, filtration or centrifugal separation may be used.

The filtration method among methods for removing microorganisms sludge in step b) is not particularly limited, and any method known in the related art may be used. Preferably, membrane filtration may be used.

Membrane filtration is not particularly limited, and any method known in the related art may be used. In one example of the membrane filtration method, the fermentation broth prepared from an L-glutamic acid producing strain is filtered through a ceramic membrane filter having a pore size of about 0.1 μm while applying pressure in a perpendicular direction to the flow of the fermentation broth to remove microorganism sludge. In the course of removing microorganism sludge, in order to minimize the amount of L-glutamic acid remaining in the microorganism sludge, the microorganism sludge may be treated by Dia filtration step, wherein the microorganism sludge is re-diluted with purified water and filtered. This procedure may be carried out at 50° C. to 60° C. in order to enhance efficiency of the membrane filtration.

After step b), the fermentation liquor may be concentrated. The concentration procedure is not particularly limited, and any method known in the related art may be used. In one example of the concentration procedure, the fermentation liquor filtered through the membrane may be concentrated using a rotary evaporator in a solid content concentration of about 20 to 50%, more preferably 35 to 45%. In order to prevent browning of the fermentation liquor in the course of the above procedure, the inside of the evaporator may be preferably maintained at high vacuum.

In step c), the methods for drying the fermentation liquor from which the microorganism sludge is removed are not particularly limited, and any method known in the related art may be used. In one example of the drying method, the fermentation liquor from which the microorganism sludge is removed may be dried using a spray dryer or a granulation dryer under aseptic conditions. This procedure is preferably performed at 100° C. to 110° C.

In another aspect, the present invention provides a flavoring containing L-glutamic acid derived from natural foods produced by the method of the present invention.

The flavoring containing L-glutamic acid derived from natural foods may contain moisture preferably in an amount of 0.5 wt % to 5 wt %, more preferably 0.5 wt % to 3 wt %, based on the total weight of the flavoring. Within the range, spoilage of the flavoring during transport and/or distribution can be prevented and thus there is an advantage of securing the storage period of the flavoring for a long time.

Next, the present invention will be illustrated in more detail with reference to examples and comparative examples. However, it should be understood that the following examples and comparative examples are provided for illustration only, and are not to be in any way construed as limiting the present invention.

Comparative Example 1

Drying of Fermentation Liquor Using Ammonia as pH Modifier (1) Cultivation of L-Glutamic Acid Producing Strain 1) Preparation of Culture Medium

*Corynebacterium glutamicum* KFCC-11113 capable of producing L-glutamic acid in high concentration (a variant obtained from *Corynebacterium glutamicum* KFCC-10656 by treatment with N-methyl-N'-nitro-N-nitrosoguanidine (NTG)) was cultured in a culture medium prepared as described below. The components used in preparation of the culture medium were all food grade.

Primary seed culture medium: The primary seed culture medium containing 1% of glucose 1% of yeast extract, 0.25% of sodium chloride, 0.1% of urea and 0.1% of ammonium chloride, pH 7.0 was prepared.

Secondary seed culture medium: The secondary seed culture medium containing 5% of raw sugar, 1% of yeast extract, 0.2% of monopotassium phosphate, 0.05% of magnesium sulfate, 0.002% of iron sulfate, 1 mg/l of biotin, 2 mg/l of thiamine hydrochloride, 0.001% of manganese sulfate, 0.001% of zinc sulfate and a small amount of antifoaming agent, pH 7.0, was prepared.

Fermentation medium: The fermentation medium containing 8% of raw sugar, 0.5% of yeast extract, 0.2% of monopotassium phosphate, 0.05% of magnesium sulfate, 0.002% of iron sulfate, 1 mg/l of biotin, 2 mg/l of thiamine hydrochloride, 0.001% of manganese sulfate, 0.001% of zinc sulfate and a small amount of antifoaming agent, pH 7.2, was prepared.

2) Cultivation of Microorganisms Using Ammonia as a pH Modifier 50 ml of the primary seed culture medium was plated in a 500 ml Erlenmeyer flask for stirring, which was subjected to autoclaving at 121° C. for 20 minutes and then cooled. To this end, Corynebacterium glutamicum KFCC-11113 was inoculated and shake cultured at 30° C. and 200 revolutions per minutes for 20 hours.

2 L of the secondary seed culture medium was placed in a 5 L test fermenter, which was subjected to autoclaving at 121° C. for 20 minutes and then cooled. To this end, 150 ml of the primary seed culture medium was inoculated and cultured at 30° C. and 900 rpm for 18 hours while supplying 2 L of air per minute.

2 L of the fermentation medium was placed in a 5 L test fermenter, which was subjected to autoclaving at 121° C. for 20 minutes and then cooled. To this end, 300 ml of the secondary seed culture medium was inoculated and cultured at 30~39° C. and 900 rpm while supplying 2 L of air per minute.

While culturing under the above conditions, a nonionic surfactant was added in a concentration of 0.01%~0.5% between the early stage and end stage of the exponential phase of the growth curve of Corynebacterium glutamicum KFCC-11113. To the fermentation broth, 28% of aqueous ammonia was added so that the pH of the fermentation broth during the cultivation was 7.0~7.8. When the concentration of residual sugars during cultivation reached 0.5~1.5%, sterilized raw sugars were frequently added so that the total sum of the sugars added was 18% on the basis of the amount of fermentation broth. After completion of cultivation, the residual amount of ammonia was 15.2 g/L and the concentration of L-glutamic acid was 102 g/L.

(2) Purification and Drying of Fermentation Liquors in which Ammonia was Used

Figure 2:
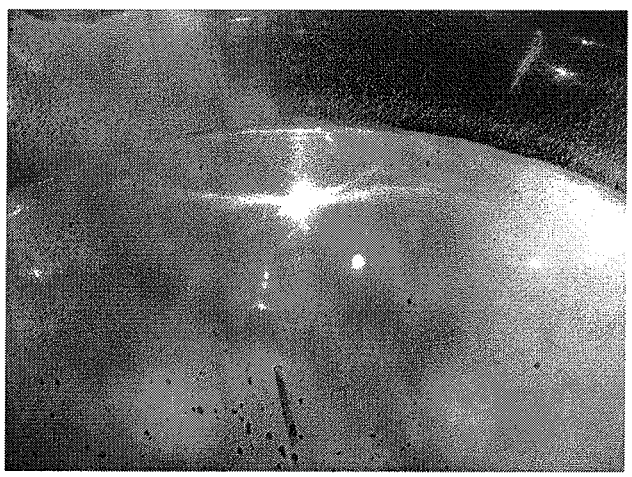
FIG. 2 is a graph of a fermentation liquor of Comparative Example 1, wherein drying of the fermentation liquor is not achieved though spray drying is performed.

The fermentation broth, after the completion of culturing, was filtered through a ceramic membrane having a pore size of 0.1 μm to remove microorganism sludge. The filtered liquor was concentrated by a rotary evaporator so that the solid content concentration became 40%. After that, drying of the concentrated liquor was attempted at about 100° C. by means of a spray dryer. However, most of the fermentation liquor was coated on the bottom of the spray dryer, which failed to produce normal dried products (FIG. 2).

Additionally, to the liquors from which microorganism sludge was removed, an activated carbon for food was added in 0.5 wt %, 1.0 wt %, and 2.0 wt %, respectively, were left at 50° C. for one hour and then filtered through a 0.5 μm filter paper to remove color additive impurities. Subsequently, the obtained filtered liquor was concentrated by means of a rotary evaporator so that the solid content was 40%. After that, drying of the concentrated liquor was attempted by means of a spray dryer. However, drying could not be achieved.

Example 1

Drying of Fermentation Liquors in which pH Modifier was Replaced with Sodium Hydroxide at Different Times
(1) Cultivation of L-Glutamic Acid Producing Strains
1) Preparation of Culture Medium The same three culture media were prepared in the same manner as in 1) of (1) of Comparative Example 1.

2) Cultivation of Microorganisms in which pH Modifier was Replaced with Sodium Hydroxide at Different Time The microorganisms were cultured in the same manner as in 2) of (1) of Comparative Example 1 except that the pH modifier in the three culture media was replaced with 33% sodium hydroxide at different time instead of using 28% aqueous ammonia continuously as a pH modifier.

The time for replacing the pH modifier in the three culture media was 10, 15 and 20 hours after culturing of microorganism, respectively, wherein 28% aqueous ammonia as a pH modifier was replaced with 33% sodium hydroxide. (See FIG. 1).

(2) Purification and Drying of Fermentation Liquors in which Sodium Hydroxide was Replaced at Different Time The fermentation liquors were purified and dried in the same manner as in (2) of Comparative Example 1.

Table 1 summarizes the results of measuring the content of L-glutamic acid in the final fermentation broth, the content of residual ammonia and drying efficiency of the fermentation liquors, and the moisture content of dried products in Comparative Example 1 and Example 1.

TABLE 1

| | Comparative Example 1 | Example 1 | | |
|---|---|---|---|---|
| | | Replacement time | | |
| | Not replaced | After 10 hours | After 15 hours | After 20 hours |
| L-glutamic acid (g/L) | 102 | 77 | 95 | 98 |
| Residual ammonia (g/L) | 15.2 | 0 | 2.2 | 7.2 |
| Drying efficiency | Not dried | Very good | Very good | Good |
| Moisture content in dried products (%) | Not dried | 1.1 | 1.3 | 5.0 |

As indicated in Table 1, it was found that, in the case of the fermentation liquor in which ammonia was continuously used as a pH modifier without exchange, there was a significant amount of residual ammonia in the final fermentation broth. It was determined that the residual ammonia was bound to L-glutamic acid, forming ammonium salts in the fermentation liquor, which inhibited drying of the fermentation liquor.

On the contrary, it was found that, in the case of replacing ammonia with sodium hydroxide as a pH modifier, the drying efficiency of the fermentation liquor became very high, owing to the fact that the sodium salt did not inhibit drying of the fermentation liquor unlike ammonium salt.

Residual ammonia concentration was reduced as the time of addition of aqueous ammonia, as a pH modifier, was lowered through replacement with sodium hydroxide. However, when the aqueous ammonia was replaced with sodium hydroxide 10 hours after culturing of microorganisms, the production amount of L-glutamic acid was little. From this result, it was determined that, considering the fact that ammonia could act as a pH modifier as well as a nitrogen source, the replacement of the aqueous ammonia with sodium hydroxide as a pH modifier at an early stage of the culturing when microorganisms were ready to grow or vigorously growing could cause insufficient supply of nitrogen sources, thereby adversely affecting the fermentation of L-glutamic acid.

Further, it was found that the lower the content of residual ammonia in the final fermentation broth was, the higher the drying efficiency was.

It was determined that the suitable time for replacing ammonia with sodium hydroxide was around 15 hours after culturing because it did not inhibit the fermentation of L-glutamic acid and drying efficiency was high.

Example 2

Drying of the Fermentation Liquors in which Sodium Hydroxide was Used as a pH Modifier (1) Cultivation of L-Glutamic Acid Producing Strains 1) Preparation of Culture Media The culture media were prepared in the same manner as in 1) of (1) of Comparative Example 1.

2) Cultivation of Microorganisms in which Sodium Hydroxide was Used as a pH Modifier The microorganisms were cultured in the same manner as in 2) of (1) of Comparative Example 1 except that 33% sodium hydroxide was used as a pH modifier instead of 28% aqueous ammonia and additional ammonium sulfate was supplemented as a separate nitrogen source.

Table 2 summarizes the results of measuring the content of L-glutamic acid in the final fermentation broth and the content of residual ammonia.

TABLE 2

|  | Added amount of ammonium sulfate (g/L) | | | | |
| --- | --- | --- | --- | --- | --- |
|  | 20 | 40 | 50 | 60 | 80 |
| L-glutamic acid (g/L) | 47 | 86 | 98 | 96 | 93 |
| Residual ammonia (g/L) | 0 | 0 | 1.1 | 4.0 | 9.3 |

As is apparent from Table 2, it was found that, in the case of using sodium hydroxide as a pH modifier from an early stage of culturing, a separate nitrogen source must be added in order to conduct efficient fermentation of L-glutamic acid. Further, in the case of using ammonium sulfate, it is preferred to add 40 g/L or more of ammonium sulfate, more preferably 50 g/L or more, still more preferably 50 to 80 g/L.

The invention claimed is:

1. A method for producing a flavoring containing L-glutamic acid, the method comprising:
    culturing an L-glutamic acid-producing microorganism in a medium containing a carbon source, a nitrogen source and a pH modifier, wherein in the culturing, initially ammonia is used as the nitrogen source as well as the pH modifier and subsequently ammonia is replaced with a pH modifier other than ammonia along with additional ammonium sulfate supplemented as a separate nitrogen source within 10-20 hours after starting the culturing such that the content of ammonia remaining in a final fermentation broth is 0 to 10 g/L;
    after culturing, removing microorganism sludge from the final fermentation broth to yield a fermentation liquor; and
    drying the fermentation liquor from which the microorganism sludge is removed.

2. The method according to claim 1, wherein the pH modifier other than ammonia is at least one selected from the group consisting of alkaline sodium salts and alkaline potassium salts.

3. The method according to claim 1, wherein the nitrogen source is at least one selected from the group consisting of ammonium salts, urea, nitrates, amino acids, peptides, proteins, yeast extracts, and corn saccharized solutions.

4. The method according to claim 1, wherein removing the microorganism sludge is performed by using filtration or centrifugal separation.

5. The method according to claim 4, wherein the filtration is membrane filtration.

6. The method according to claim 1, further comprising: producing powder or granules from the dried fermentation liquor.

7. A flavoring containing L-glutamic acid produced by the method according to claim 1.

8. The flavoring according to claim 7, wherein a moisture content of the flavoring is 0.5 wt % to 5 wt % based on the total weight of the flavoring.

9. The method according to claim 1, wherein ammonia is replaced with the pH modifier other than ammonia 10 hours after starting the culturing.

10. The method according to claim 1, wherein ammonia is replaced with the pH modifier other than ammonia 15 hours after starting the culturing.

11. The method according to claim 1, wherein the method is carried out without crystallization.

12. The method of claim 1, wherein ammonia is replaced with the pH modifier other than ammonia within 10-15 hours after starting the culture.

13. The method of claim 1, wherein 40-80 g/L ammonium sulfate is added.

14. The method of claim 13, wherein 50-80 g/L ammonium sulfate is added.

15. The method of claim 14, wherein yield of L-glutamic acid is 93-98 g/L.

* * * * *